United States Patent [19]
Satzinger et al.

[11] 3,966,813
[45] June 29, 1976

[54] PROCESS FOR THE PREPARATION OF 1-(m- AND P-HYDROXYPHENYL)-2-AMINOETHANOL

[75] Inventors: Gerhard Satzinger; Wolfgang Dieter Herrmann, both of Denzlingen, Germany

[73] Assignee: Warner-Lambert Company, Morris Plains, N.J.

[22] Filed: June 20, 1972

[21] Appl. No.: 264,698

[30] Foreign Application Priority Data
June 21, 1971 Germany............................ 2130710

[52] U.S. Cl............................ 260/570.6; 260/566 A
[51] Int. Cl.²......................................... C07C 85/11
[58] Field of Search.................. 260/570.5 C, 570.6

[56] References Cited
UNITED STATES PATENTS

| | | |
|---|---|---|
| 1,877,795 | 9/1932 | Bockmuhl et al................ 260/570.6 |
| 1,995,709 | 3/1935 | Hartung........................... 260/570.6 |
| 2,505,645 | 4/1950 | McPhee............................ 260/570.6 |
| 3,028,429 | 4/1962 | Wilbert et al.................... 260/570.6 |
| 3,088,978 | 5/1963 | Brunner et al...................... 260/580 |
| 3,253,034 | 5/1966 | McLoughlin...................... 260/570.6 |
| 3,634,519 | 1/1972 | Bentz et al...................... 260/571 X |

*Primary Examiner*—Robert V. Hines
*Attorney, Agent, or Firm*—Albert H. Graddis; Frank S. Chow; George M. Yahwak

[57] ABSTRACT

The present invention relates to a process for the preparation of 1-(m- and p- hydroxyphenyl)-2-aminoethanol which consists of converting an m- or p-hydroxyacetophenone to an isonitrosoketone followed by hydrogenation of the isonitrosoketone. These compounds are sympathomimetics which produce vasoconstricting and cardiotonic effects.

5 Claims, No Drawings

PROCESS FOR THE PREPARATION OF 1-(M- AND P-HYDROXYPHENYL)-2-AMINOETHANOL 1-(m- and p-hydroxyphenyl)-2-aminoethanol (I and II) form part of the group of pharmaceuticals of sympathomimetics and are commonly used for the treatment of circulatory insufficiency, hypotension, and states of shock because of their vasoconstricting and cardiac action stimulating effect.

"Organic Reactions", vol. 7, John Wiley & Son, New York, 1953, pages 327–377. The methods by which the isonitroso group has previously been introduced into ketones is unsuited for the synthesis of the m-hydroxy-isonitrosoacetophenone; preparation of this potentially important intermediate product could not yet be realized. In principle, it was possible to make the p-hydroxy-isonitrosoacetophenone (see Karg, Arch.P-harm. 282, 49 (1944)), but the method used is techni-

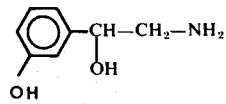

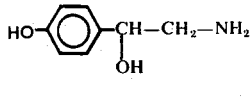

I

II

Prior processes for the preparation of the compounds of the present invention have utilized, as starting compounds, suitable hydroxyacetophenones which can be converted to the aminoalcohols in five or six steps. (R. Sachs, French Pat. No. 856,296 of 9/14/38, corresponding DBP [German Federal Pat. No.] 913,779 Kl.12q of 11/16/38, published 8/9/54; H. Legerlotz, Swedish Pat. 99,623 of 9/14/39, published 8/20/40, French Priority 9/14/38; A. D'Amico, L. Bertolini and C. Monreale, Chimica e industria (Milan) 38, 93 (1956)).

Another synthesis uses hydroxybenzoic acids or their chlorides as starting materials. This synthesis requires five steps to obtain the aminoalcohols. (G. Zolss, Sci. Pharm. 32, 76 (1964); Ger. P. (East) 50,624 Kl.C 07c, of 10/5/66).

The total yields obtained when proceeding according to the two procedures described above are between 20 % and 30 %. The present invention relates to a technically advanced process for preparing the compounds I and II which has only two steps and by which a total yield of 70 to 80 % is obtained. The process according to the invention consists of converting the m- or p-hydroxyacetophenone into the corresponding isonitrosoketone by reaction with agents capable of introducing the nitroso group into the compound and catalytically hydrogenating the isonitrosoketone to obtain the desired end products. The reaction proceeds as below:

cally unsatisfactory as to yield and purity of the end product and as to the safety measures required. Most surprisingly, it has now been found that under the catalytic influence of hydrogen chloride a nearly quantitative reaction of the two hydroxyacetophenones with alkylnitrites to the corresponding isonitrosoacetophenones takes place in certain solvents which were previously not used for this reaction. The solvents concerned are dipolar aprotic solvents, i.e. solvents which have a high dielectric constant and a high dipole moment but no acid hydrogen atoms. Dimethyl sulfoxide (DMSO), acetonitrile, dimethyl formamide (DMF), dimethyl acetamide and hexamethyl phosphoric acid triamide (HMPT), are exemplary. The success of this reaction in the above solvents is obviously connected with a stabilization of the end products which are normally decomposed under the reaction conditions of the prior art; the results described for the solvents used in the prior art, i.e. no reaction or reaction with secondary reactions (or side reactions) does not occur in the process of the present invention. To our present knowledge, the stabilization of the isonitroso compounds, according to the invention, in dipolar aprotic solvents is attributable to the formation of donor-acceptor complexes between molecules of the solvent and of the isonitrosoacetophenone. The infrared spectra of such solutions clearly show shifts, in particular in the frequency range of —C=O— and —C=N—, which suggest formation of adducts with salt structure. The com-

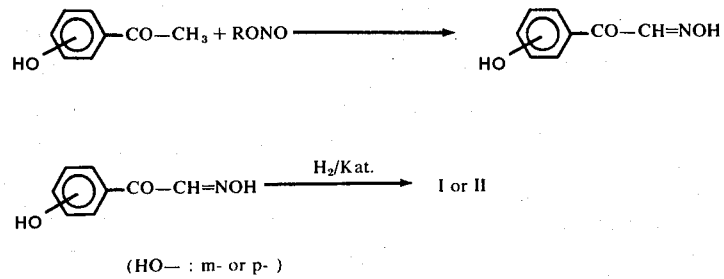

(HO— : m- or p- )

L. Claisen and O. Manasse (Ber. Otsch.Chem.Ges. 20, 656, 2194 (1887)) were the first to describe the preparation of aliphatic isonitrosoketones by means of amylnitrite under alkaline or acid catalysis O. Touster gives a summary survey of further investigations in plex from HMPT and m-hydroxy-isonitrosoacetophenone is sufficiently stable that it can be isolated as a crystalline compound from the reaction mixture of the reaction between m-hydroxyacetophenone and isoamylnitrite in HMPT. This molecular compound contains 1 mole of HMPT per mole of isonitroso compound, possesses a defined melting point (65°C) and can be recrystallized from different solvents in the undecomposed state. The adducts of the isonitroso compounds, according to the invention, with other dipolar aprotic solvents are more unstable and disintegrate during (aqueous) processing of the reaction batches. The reaction between m- or p-hydroxyacetophenone and the alkyl nitrite can be carried out at temperatures in the range between −30°C and the boiling point of the alkyl nitrite used; optimum yields being obtained at +10° to 40°C. The amount of the hydrogen chloride added has a certain influence on the course of the reaction, the best results being obtained with 0.5 to 1.2 equivalents, related to the ketone used. The reaction velocity also depends on the solvent used, it somewhat decreases in the following sequence:

HMPT> Dimethylacetamide > DMF > DMSO > Acetonitrile.

This sequence corresponds approximately to the different donor strength of the solvents. All low nitrites are suitable as alkyl nitrites; the gaseous methyl and ethyl nitrites because of their toxicity and the danger of inflammability, must be used with caution. According to the invention, the isonitroso-hydroxyacetophenones are prepared as follows: While stirring, the alkyl nitrite is slowly poured into the solution of the hydroxyacetophenone and the corresponding amount of hydrogen chloride in a dipolar aprotic solvent, the temperature preferably being 10°–40°C. The addition being finished, stirring is continued for some hours. The reaction mixture is subsequently poured into ice water while stirring. The isonitroso compound is then extracted with an organic solvent that is not miscible with water; the organic phase is separated, washed, clarified with charcoal, dried and the solvent is distilled off. In order to decompose the molecular compound, when using HMPT as the solvent, the compound is dissolved in an aqueous base, treated with chloroform. The aqueous alkaline phase is acidified and extracted. The isonitrosoacetophenones are thus obtained with a yield of 70–95 %. Isonitrosoacetophenone hydrogenation to he hydroxyphenyl-ethanolamines of formulae I or II has not been described in the literature. It is effected however, in a manner known in principle under the catalysis of palladium, the isonitroso and keto group being reduced either simultaneously or successively. Proceeding according to invention, it is, therefore, possible to prepare the medically valuable 1-(hydroxyphenyl)-2-amino-ethanols, with simple chemical and technical means in a two-step synthesis and with high yields, from the commercially available m- and p-hydroxyacetophenones.

The process according to the invention is described in detail in the following examples.

EXAMPLE 1

680 g (5 moles) of technical, about 95% m-hydroxyacetophenone are dissolved in 1.5 l of HMPT in a 6 l round-bottomed flask provided with stirrer, reflux condenser, thermometer and dropping funnel. Then a solution of 91 g (2.5 moles) of hydrogen chloride in 1.5 l of HMPT is prepared and added to the above solution. The contents of the flask are cooled to +10°C and then 644 g (5.5 moles) of isoamyl nitrite are poured into the solution within approximately 30 minutes; the temperature should not exceed 20°C. As the reaction is faintly exothermic, it may be necessary to cool while adding. The addition being finished, stirring is effected for 5–6 hrs. at 15°–20°C. While stirring, the reaction mixture is poured into 15 l of ice water, and the oxime is extracted three times with 3 l of benzene. The combined benzene extracts are washed with 8 l of ice water, mixed thoroughly with 50 g of activated charcoal and 300 g of anhydrous sodium sulfate, and filtered. Then the benzene solution is extracted three times with portions of 6 l of ice-cold 5% ammonium hydroxide solution; the combined aqueous phases are then extracted three times with portions of 3 l of chloroform in order to remove the HMPT still present. While cooling the aqueous phase is acidified with acetic acid until the pH is 5–6 and the oxime is extracted three times with portions of 3 l of ethyl acetate. After drying with sodium sulfate and clarifying with activated charcoal, the solvent is distilled off under reduced pressure; the remaining oily residue crystallizes either spontaneously or upon being seeded. It is dried at 40°–50°C, 640 g = 81.5 % of theoretical amount of m-hydroxy-isonitrosoacetophenone are obtaind. The substance forms yellowish crystals having a m.p. of 114°–5°C.

Elementary analysis: $C_8H_7NO_3$ MG 165,15 Calc.: C: 58.18, H: 4.28, N: 8.48, O: 29.06; Found: C: 58.37 H: 4.29 N: 8.49 O: 28.72. UV-spectrum: $\eta_{max}^{MeOH} = 323$, 264, 238, 219 nm; $\epsilon = 2400, 8800, 11400, 13800$.

EXAMPLE 2

680 g (5 moles) of m-hydroxyacetophenone are dissolved in 2.5 l of dimethylformamide which contains 191.5 g (5.25 moles) of hydrogen chloride. Within 3–4 hrs., a mixture of 540 g (5.25 moles) of tertiary butyl nitrite and 540 ml of dimethylformamide is poured into this solution at 30°–40°C. This mixture is stirred for some hours or allowed to stand overnight. While stirring, the reaction mixture is poured into 30 l of ice water, extracted three times with ethyl acetate, and the organic phase is washed twice with water. The solution of the isonitroso compound in ethyl acetate is dried over calcium chloride, stirred with activated charcoal for half an hour and then filtered. The solvent is distilled off in vacuo, and the crystalline residue recrystallized from 2 l of toluene + 0.6 l of dioxane. The yield of m-hydroxy-isonitrosoacetopheneone is 750 g = 91 % of theory.

EXAMPLE 3

136.15 g (1 mole) of m-hydroxyacetophenone and 38.4 g of hydrogen chloride (1.05 moles) are dissolved in 500 ml of dimethyl sulfoxide. A mixture of 108 g of tertiary butyl nitrite (1.05 moles) and 108 ml of DMSO is poured into this solution within 2 hrs; the temperature kept at 15°–20°C. Stirring is effected for some hours. The reaction mixture is poured into 8 l of ice water. Further processing is effected as described in Example 2. The yield of m-hydroxy-isonitrosoacetophenone is 120 g = 73 % of theory.

EXAMPLE 4

Analogous to Example 3, but using dimethylacetamide as the solvent. The yield amounts to 134 g = 81 % of theory.

Hydrogenation to 1-(m-hydroxyphenyl)-2-aminoethanol 165.15 g (1 mole) of m-hydroxy-isonitrosoacetophenone are dissolved in 1.5 l of 70% ethanol and treated with 250 ml of 37% hydrochloric acid and 60 g of Pd charcoal (10%). Hydrogenation is effected while shaking at 30°–50°C until no more hydrogen is taken up. During 8 hrs., 70 l (theory: 72 l) of hydrogen are taken up. The hydrogenation solution is filtered off from the catalyst and evaporated to dryness in a vacuum. The remaining residue is recrystallized from methanol/ethyl acetate. The yield is 165 g (87 % of theory) of 1-(m-hydroxyphenyl)-2-aminoethanol hydrochloride. m.p. 158°–9°C.

EXAMPLE 5

39.55 g (1.08 moles) of hydrogen chloride are dissolved in 625 ml of HMPT, and 136.25 g (1 mole) of p-hydroxyacetophenone are added. The solution is cooled to 10°C and 128.8 g (1.1 mole) of isoamyl nitrite are added within 10 minutes. Stirring is continued for 6 hrs. at 15°–20°C. Processing is effected as in Example 1 by pouring into water, extracting with benzene, extracting with ammonia solution etc. Finally, it is recrystallized from 1 l of water. The yield of p-hydroxy-isonitrosoacetophenone is 127 g = 77 % of theory; m.p. 163°–5°C.

EXAMPLE 6

136.15 g (1 mole) of p-hydroxyacetophenone and 40 g (1.1 mole) of hydrogen chloride are dissolved in 500 ml of DMF and, while stirring at 40° ± 2°C, mixed within two hours with a solution of 113.5 g (1.1 mole) of tertiary butyl nitrite in 115 ml of DMF. The addition being finished, stirring is continued for 3 hrs. and then the solution poured into 5 l of cold water. The isonitroso compound is extracted with ethyl acetate, and the organic phase is washed with water and treated with calcium chloride and activated charcoal. Following filtration, the solvent is distilled off in vacuo. The yield is 147 g = 89 % of theoretical amount of p-hydroxyisonitrosoacetophenone, m.p. 163°–165°C.

What is claimed is:
1. A two-step process for the preparation of 1-(hydroxyphenyl)-2-aminoethanol which comprises:
    A. reacting in a dipolar aprotic solent, hydroxyacetophenone with a lower alkyl nitrite in the presence of a hydrogen chloride catalyst, to form isonitrosoacetophenone, and
    B. catalytically reacting the isonitrosoacetophenone with palladium to cause hydrogenation and bring about the reduction of the isonitroso and keto moieties on the isonitrosoacetophenone molecule.
2. A process as set forth in claim 1 wherein the dipolar, aprotic solvent is selected from the group consisting of hexamethyl phosphoric acid triamide, dimethylformamide, dimethylacetamide, dimethyl sulfoxide and acetonitrile.
3. A process as set forth in claim 1 wherein the lower alkyl nitrite has the formula RONO wherein the alkyl group R contains from 1 to 5 carbon atoms.
4. A process as set forth in claim 1 wherein the reaction of hydroxyacetophenone with a lower alkyl nitrite takes place at a temperature in the range of from −30° to 100°C.
5. In a two-step process for the preparation of 1-(hydroxyphenyl)-2-aminoethanol which comprises reacting hydroxyacetophenone with a lower alkyl nitrite to give isonitrosohydroxyacetophenone, the steps which comprise:
    A. carrying out said reaction in the presence of a dipolar aprotic solvent, and
    B. catalytically hydrogenating the isonitrosohydroxyacetophenone so formed, so as to reduce the isonitroso and keto moieties on the isonitrosoacetophenone molecule, into the corresponding 1-(hydroxyphenyl)-2-aminoethanol.

* * * * *